(12) United States Patent
Wittland et al.

(10) Patent No.: US 10,653,848 B2
(45) Date of Patent: May 19, 2020

(54) SAFETY DEVICE FOR A SYRINGE

(71) Applicants: Gerresheimer Regensburg GmbH, Regensburg (DE); Gerresheimer Bunde GmbH, Bunde (DE)

(72) Inventors: Frank Wittland, Enger (DE); Maximilian Vogl, Mantel (DE)

(73) Assignees: Gerresheimer Regensburg GmbH, Regensburg (DE); Gerresheimer Bunde GmbH, Bunde (DE)

( * ) Notice: Subject to any disclaimer, the term of this patent is extended or adjusted under 35 U.S.C. 154(b) by 164 days.

(21) Appl. No.: 15/573,047

(22) PCT Filed: May 9, 2016

(86) PCT No.: PCT/EP2016/060279
§ 371 (c)(1),
(2) Date: Nov. 9, 2017

(87) PCT Pub. No.: WO2016/202498
PCT Pub. Date: Dec. 22, 2016

(65) Prior Publication Data
US 2018/0161512 A1    Jun. 14, 2018

(30) Foreign Application Priority Data
Jun. 15, 2015 (EP) ..................... 15172173

(51) Int. Cl.
*A61M 5/32* (2006.01)
*A61M 5/31* (2006.01)

(52) U.S. Cl.
CPC .......... *A61M 5/3202* (2013.01); *A61M 5/326* (2013.01); *A61M 5/3272* (2013.01);
(Continued)

(58) Field of Classification Search
CPC ........ A61M 5/3202; A61M 2005/3217; A61M 5/3272
See application file for complete search history.

(56) References Cited

U.S. PATENT DOCUMENTS 5,591,138 A    1/1997  Vaillancourt
6,186,980 B1   2/2001  Brunel
(Continued)

FOREIGN PATENT DOCUMENTS

DE    112009001083 T5    3/2011
WO    WO 2001/054758 A1  8/2001
(Continued)

OTHER PUBLICATIONS

International Search Report with Written Opinion corresponding to International Patent Application No. PCT/EP2016/060279, dated Aug. 10, 2016.
(Continued)

*Primary Examiner* — Nathan R Price
*Assistant Examiner* — Melissa A Snyder
(74) *Attorney, Agent, or Firm* — Leydig, Voit & Mayer, Ltd.

(57) ABSTRACT

The invention relates to a safety device for a syringe for avoiding stab wounds, said syringe having a syringe body and a piercing means arranged on the distal end of the syringe body. The safety device comprises a sleeve element that extends along an axial direction (X) and encloses at least partly the piercing means and the syringe body, and a collar element that can be arranged on a distal end region of the syringe body and locks the safety device in the axial direction (X), said collar element having at least one guide projection which engages at least one guide track of the sleeve element. The safety device is further characterized by having a cap element that can be arranged at least in sections
(Continued)

on top of the sleeve element and by means of which the sleeve element can be locked with respect to the movement of the syringe body relative to the sleeve element.

13 Claims, 6 Drawing Sheets

(52) U.S. Cl.
CPC .............. *A61M 2005/312* (2013.01); *A61M 2005/3107* (2013.01); *A61M 2005/3118* (2013.01); *A61M 2005/3267* (2013.01)

(56) References Cited

U.S. PATENT DOCUMENTS

| | | | |
|---|---|---|---|
| 8,048,035 B2 | 11/2011 | Mesa et al. | |
| 9,907,916 B2* | 3/2018 | Evans | A61M 5/3272 |
| 2004/0204678 A1* | 10/2004 | Popovsky | A61M 5/326 |
| | | | 604/110 |
| 2005/0165353 A1 | 7/2005 | Pessin | |
| 2007/0100290 A1* | 5/2007 | Schiffmann | A61M 5/3202 |
| | | | 604/198 |
| 2009/0005742 A1* | 1/2009 | Liversidge | A61M 5/326 |
| | | | 604/263 |
| 2011/0118667 A1* | 5/2011 | Zaiken | A61M 5/3202 |
| | | | 604/138 |
| 2011/0137261 A1 | 6/2011 | Garber et al. | |
| 2013/0035645 A1* | 2/2013 | Bicknell | A61M 5/20 |
| | | | 604/198 |
| 2013/0324934 A1 | 12/2013 | Holmqvist et al. | |
| 2014/0257200 A1 | 9/2014 | Auerbach et al. | |
| 2015/0032062 A1* | 1/2015 | Jakob | A61M 5/3216 |
| | | | 604/198 |
| 2016/0008553 A1 | 1/2016 | Fournier et al. | |
| 2016/0067421 A1* | 3/2016 | Ogawa | A61M 5/283 |
| | | | 604/194 |
| 2018/0104421 A1 | 4/2018 | Wittland et al. | |
| 2018/0110934 A1 | 4/2018 | Wittland et al. | |
| 2018/0133409 A1 | 5/2018 | Fraas et al. | |
| 2018/0161511 A1 | 6/2018 | Fraas et al. | |
| 2018/0161516 A1 | 6/2018 | Wittland et al. | |

FOREIGN PATENT DOCUMENTS

| | | |
|---|---|---|
| WO | WO 2012/096620 A1 | 7/2012 |
| WO | WO 2014/131987 A1 | 9/2014 |

OTHER PUBLICATIONS

Canadian Office Action, dated May 9, 2018, in Canadian Patent Application No. 2,984,417, a related application, 1 pp.
Indian Examination Report with English translation, dated Oct. 22, 2019, corresponding to Indian Patent Application No. 201727040481, 3 pp.

* cited by examiner

SAFETY DEVICE FOR A SYRINGE

CROSS-REFERENCE TO RELATED APPLICATIONS

This application is a U.S. National Stage Application under 35 U.S.C. § 371 of International Application No. PCT/EP2016/060279, filed May 9, 2016, which claims the benefit and priority of European Patent Application No. 15172173.5, filed Jun. 15, 2015, both of which are hereby incorporated by reference in their entirety to the extent not inconsistent herewith.

The invention relates to a safety device for avoiding stab wounds for a syringe having a syringe body and a piercing means arranged at the distal end of the syringe body, comprising a sleeve element, which extends along an axial direction (X) and at least partially encloses the piercing means and the syringe body, and a collar element, which can be arranged on a distal end region of the syringe body and locks the safety device in the axial direction (X), the collar element comprising at least one guide projection, which engages in at least one guide track of the sleeve element.

Generic safety devices for avoiding stab wounds are known from the prior art. The use of safety devices of this kind is meaningful in particular in the case of pre-filled syringes. The handling of such syringes is very simple, as the medium does not have to be transferred into the syringe prior to application. Furthermore, the likelihood of using an incorrect medicine is very low, even in emergencies. For vaccines and countless other medicines they are now the first-choice primary packaging material. These syringes are usually manufactured from glass or plastics material (for example COC, COP) and need to be equipped with protective caps in order to prevent damage to and/or contamination of the cannula before the syringe is used. Moreover, it is important to secure the cannula after the syringe has been used, in order to avoid stab wounds. In this case, careless replacement of the protective cap on the cannula can cause stab wounds. Often, the corresponding protective cap can no longer be found, or replacement of said cap is forgotten, which results in an avoidable risk of injury.

Accordingly, needle guards have been developed that are rigidly connected to the syringe and automatically receive the needle again after the syringe has been used. A needle guard of this kind is disclosed in DE 11 2009 001 083 T5 for example. Said document discloses a spring-driven safety sleeve which, when extended, surrounds the cannula and prevents said cannula from causing injury to the user. The safety sleeve has a curved track in which at least one guide pin moves, as a result of which it is possible to achieve different positions of the safety sleeve according to the needle tip. In this case, the at least one guide pin has to be fastened to the front geometry of the syringe by means of a collar, or has to be rigidly connected to the syringe in another manner. In order to prevent tampering or incorrect use, it should not be possible, or it should be possible only with difficulty, to remove the collar comprising the guide pin from the syringe comprising a cannula. Accordingly, a correspondingly secure fit in the axial direction is necessary.

In the field of pre-filled syringes, a protective cap or a safety device is mounted on the syringe body already prior to the filling process, in order to avoid stab wounds, and is sterilised in a standard packaging, for example in a syringe nest. Reference is also made, in this connection, to ready to use (RTU) or ready to sterilise (RTS) syringes. In general, the safety devices should be designed so as to be smooth to actuate, in order to ensure optimal comfort for the user. Accordingly, it is possible for the syringes to be actuated inadvertently even during transport. It is also possible for the syringes to be accidentally actuated during use. This may, in some circumstances, render the syringe entirely unusable. The medicine contained therein cannot be administered. Moreover, the user or the patient may likewise be injured if they inadvertently actuate the safety device.

The object of the present invention is that of providing a safety device for avoiding stab wounds for a syringe, which solves the problems mentioned at the outset.

This object is achieved by a safety device for avoiding stab wounds for a syringe having a syringe body and a piercing means arranged at the distal end of the syringe body, comprising a sleeve element, which extends along an axial direction (X) and at least partially encloses the piercing means and the syringe body, and a collar element, which can be arranged on a distal end region of the syringe body and locks the safety device in the axial direction (X), the collar element comprising at least one guide projection, which engages in at least one guide track of the sleeve element. Preferably, the guide projection is guided in the at least one guide track of the sleeve element substantially in the axial direction (X) when the sleeve element is moved relative to the syringe body. The safety device is further characterised in that said device comprises a cap element that can be arranged over the sleeve element at least in portions, and by means of which the sleeve element can be locked with respect to the movement of the syringe body relative to the sleeve element.

Since the sleeve element can be locked with respect to the movement of the syringe body relative to the sleeve element by means of the cap element, undesired protrusion of the piercing means, which may be a cannula, a needle or a lancet, through a corresponding opening in the safety device is effectively prevented. Damage to and contamination of the piercing means is accordingly prevented. The user of the syringe first has to remove the cap element from the sleeve element before the syringe can be used. The risk of inadvertent actuation is thus also reduced. It would be conceivable to apply a marking or an instruction to the cap element. The user would thus be forced to observe this marking or the instruction prior to using the syringe. A marking or an instruction of this kind could be coloured and/or haptic and/or designed in another manner.

According to a particularly preferred embodiment, the collar element is substantially formed as a hollow circular cylinder. Preferably, the circular cylinder comprises a lateral surface, on which the at least one guide projection is arranged. Preferably, the at least one guide projection extends radially away from the lateral surface. Further preferably, the guide projection is formed as a circular cylinder or as a pin. Advantageously, two diametrically opposed guide projections are arranged on the lateral surface. Accordingly, the sleeve element would also comprise two diametrically opposed guide tracks, in each of which a guide projection is guided. Preferably, the collar element is furthermore arranged on the distal end region of the syringe body so as to be rotatable in a circumferential direction (U). When the syringe is being used, the syringe, together with the safety device, is pressed against the patient's skin. The movement of the syringe body relative to the sleeve element and the guidance of the guide projection in the guide track cause the collar element to rotate along a circumferential direction (U). The sleeve element thus preferably slides over the syringe body, as a result of which the piercing means, which may be a cannula, a needle or a lancet, passes through a corresponding opening in the sleeve element. Rotation of the sleeve element on the patient's skin, about the puncture site, is thus prevented.

The syringe body is preferably designed as a hollow circular cylinder and has in its distal end region a conical end piece on which the piercing means is arranged. Preferably, a projection is formed on the conical end piece, with which projection a front face of the distal end of the collar element can engage, as a result of which the collar element, and thus the safety device, can be locked in the axial direction. Further preferably, the safety device is also substantially formed as a hollow circular cylinder.

According to a particularly preferred concept of the invention, the cap element comprises a piercing means protective device, in which the piercing means can be arranged. A piercing means protective device of this kind ensures further protection of the piercing means from damage, and in particular from contamination.

The sleeve element preferably comprises a distal opening. In this case, the internal diameter of the distal opening is preferably larger than the external diameter of the piercing means protective device at least in portions, such that the piercing means protective device can be arranged inside the sleeve element.

The piercing means protective device can preferably be brought into operative contact with the collar element, as a result of which the collar element can be locked with respect to a rotation. Operative contact of this kind may, for example, be frictional contact. It would also be conceivable, however, for the piercing means protective device and the collar element to comprise mutually corresponding latching devices which prevent rotation of the collar element.

According to a preferred embodiment, the cap element and the sleeve element comprise complementary latching elements so that the cap element and the sleeve element can be latched together in a separable manner. It would be conceivable for a latching element to comprise a predetermined breaking point which has to be broken prior to use in order to allow the cap element to be removed from the sleeve element. It would also be conceivable, however, for the latching elements to also be able to be latched in after the syringe has been used. It would thus be possible to once again arrange the cap element securely on the sleeve element after the syringe has been used, as a result of which the sleeve element would again be able to be locked with respect to the movement of the syringe body relative to the sleeve element. Accordingly, it is possible to safely dispose of the used syringe, which syringe thus no longer presents an injury risk.

According to a further preferred concept of the invention, the cap element comprises at least one wing-like element which can be received in at least one receptacle of the sleeve element. Further preferably, the cap element comprises two wing-like elements which can be received diametrically in two receptacles of the sleeve element in each case. Particularly preferably, the two wing-like elements are arranged on the cap element so as to be diametrically opposed to one another.

According to a further preferred embodiment, at least one wing-like element can be brought into operative contact with the collar element, as a result of which the collar element can be locked with respect to a rotation. Operative contact of this kind may, for example, be frictional contact. It would also be conceivable, however, for the piercing means protective device and the collar element to comprise mutually corresponding latching devices which prevent rotation of the collar element.

According to a further preferred embodiment, at least one latching element is arranged on the at least one wing-like element of the cap element, which latching element can be latched into at least one complementary latching element that is arranged in the at least one receptacle of the sleeve element.

It would also be conceivable for the sleeve element to comprise a distal region on which at least one latching element is arranged. Advantageously, the at least one latching element can be latched into at least one complementary latching element that is arranged in a distal region of the cap element.

Advantageously, the cap element is formed integrally with the piercing means protective device. Such an embodiment of the safety device has the advantage of cost-effective and simple production.

It is also conceivable, however, for the cap element to comprise a distal opening, the distal opening being formed as a receptacle, in order to receive the piercing means protective device. An embodiment of this kind makes it possible to produce the cap element and the piercing means protective device from different materials. It would accordingly be conceivable to produce the piercing means protective device from a resilient material, for example rubber. A resilient material of this kind is favourable for reducing the risk of the piercing means being damaged.

The safety device preferably comprises at least one spring element, which is operatively connected to the syringe body and counteracts the movement of the syringe body relative to the safety device. Accordingly, the cannula remains inside the sleeve element until the intended use. During use, the sleeve element has to be moved counter to the spring force in order for the cannula to be able to pass through the opening of the sleeve element. After the syringe has been used, the sleeve element automatically slides over the cannula again, driven by the spring force of the spring element. The guidance of the guide projection in the guide track causes the collar element to rotate counter to the circumferential direction (U). The user is thus protected from receiving stab wounds from the used contaminated cannula. The spring element preferably comprises a spiral spring. Other types of spring are also conceivable, however, such as leg springs or torsion springs. It would furthermore be conceivable to form the spring element as an elastomer.

According to a further advantageous concept of the invention, the at least one guide track comprises a first and a second track region, which are separated from one another by a fictive separating line extending along the axial direction (X) of the syringe body, it being possible for the guide projection to be arranged in a starting position in the first track region and to be moved from the first track region into an end position in the second track region by passing the separating line when a distal end of the piercing element is arranged at the level of the distal opening of the sleeve element as the syringe body is moved relative to the sleeve element.

Accordingly, the guide projection of the collar element can be moved from the first trackregion into the second trackregion. Said guide projection is moved when it passes a fictive separating line that separates the first and the second track regions from one another. If the guide projection is in the first track region, i.e. in a starting position, the syringe has not yet been actuated, i.e. the piercing means has not yet left the safety device. If the guide projection is in the second track region, the piercing means has already left the safety device, making injection possible. When transitioning from the first track region to the second track region, i.e. at the exact point when the guide projection passes the separating line, the distal end of the piercing means is at the level of the distal opening of the safety device.

The guide projection can preferably be moved, by means of a track of the second track region, from the second track region into an end region in which a movement of the sleeve element relative to the syringe body is at least limited, substantially in the axial direction (X). An embodiment of this kind at least limits, preferably prevents, further movement of the sleeve element relative to the syringe body. Accordingly, the piercing means is prevented from leaving the safety device again after the syringe has been used.

Other advantages, aims and properties of the present invention are explained with reference to the following description of the attached drawings. Similar components can have the same reference signs in the various embodiments.

Figure 1:
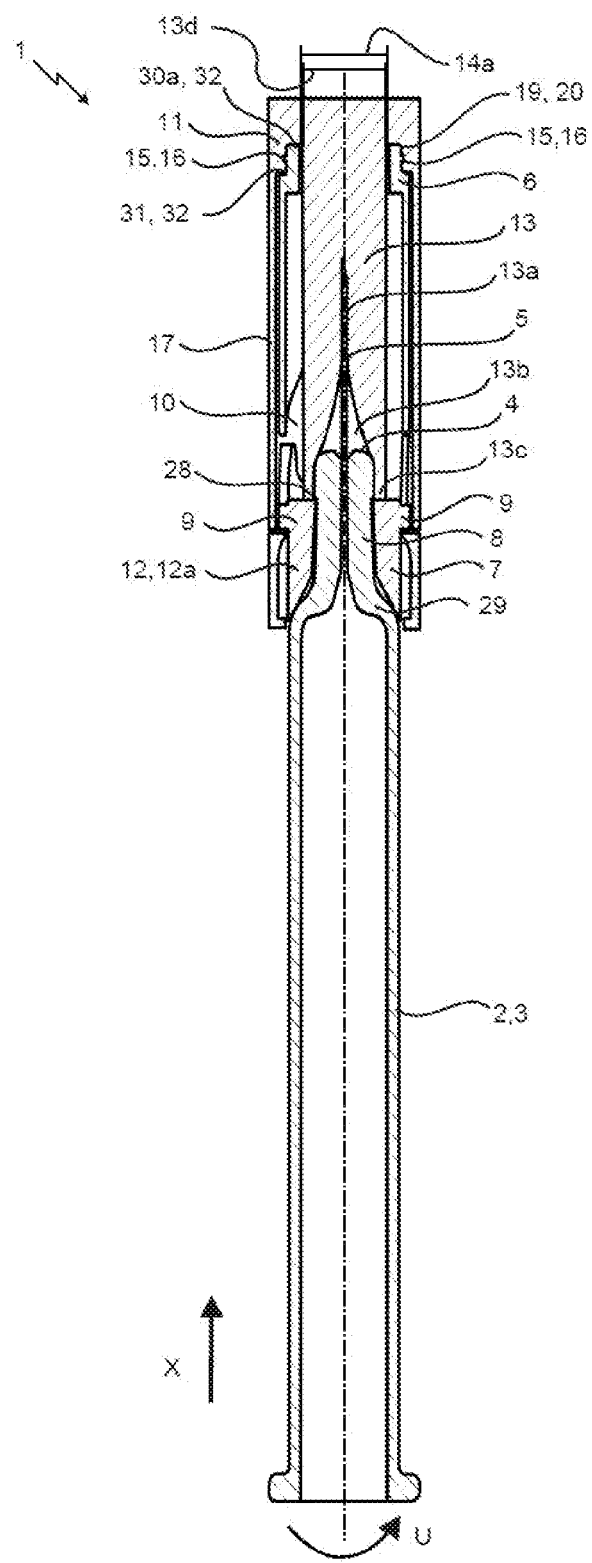
FIG. 1 is a sectional view of a syringe comprising a safety device according to an embodiment.

FIGS. 1 to 4 show a syringe (2) comprising a safety device (1) for avoiding stab wounds according to various embodiments. The syringe (2) comprises a syringe body (3) designed as a hollow circular cylinder. The syringe body has a distal end region (8) comprising a distal end (4). Arranged at the distal end (4) is a piercing means (5). This piercing means (5) is connected via a hole in the distal end region (8) to the cavity of the syringe body (3), so that the medium to be injected during application of the syringe (2) can emerge from the cavity through the piercing means (5). The distal end region (8) is designed as a conical end piece which has a smaller external diameter than the syringe body (3). The syringe also has a transition region (29) in which the external diameter of the syringe body merges into the external diameter of the end piece. Moreover, a projection (28) is arranged at the distal end region.

Figure 6:
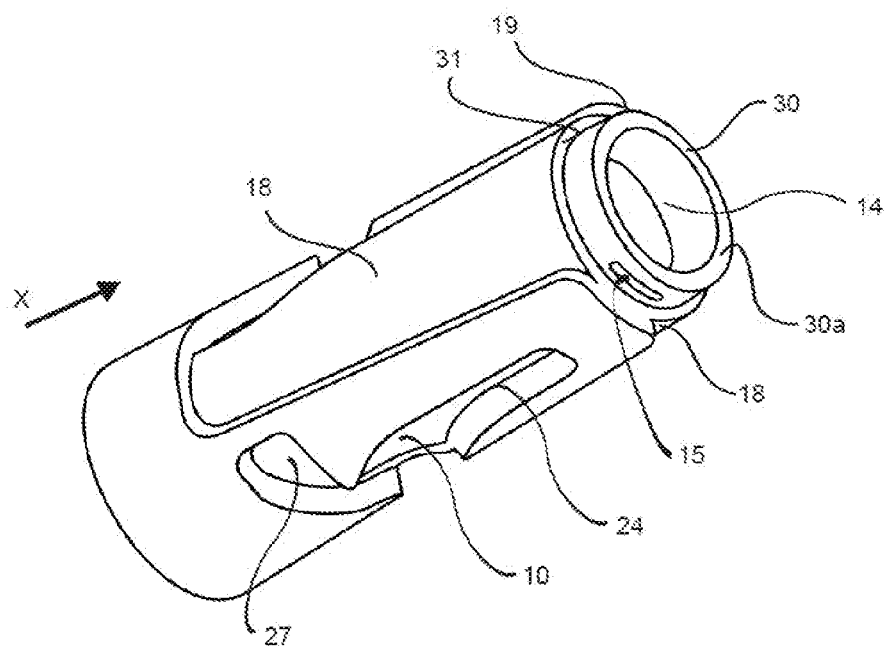
FIG. 6 is an isometric view of a sleeve element according to a further embodiment.
Figure 7:
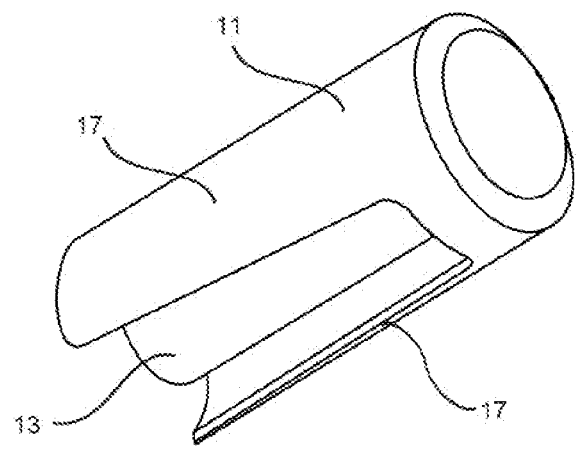
FIG. 7 is an isometric view of a cap element according to a further embodiment.
Figure 8:
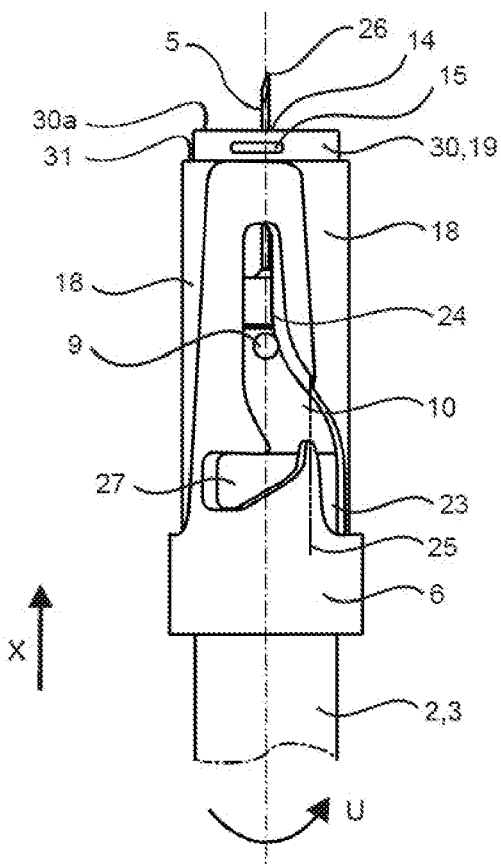
FIG. 8 is a side view of a safety device arranged on a syringe body.

Furthermore, a safety device (1) for avoiding stab wounds for a syringe (2) is shown, which syringe comprises a syringe body (3) and a piercing means (5) arranged at the distal end (4) of the syringe body (3). The safety device (1) comprises a sleeve element (6), which extends along an axial direction (X) and at least partially encloses the piercing means (5) and the syringe body (3), and a collar element (7), which is arranged on a distal end region (8) of the syringe body (3) and locks the safety device (1) in the axial direction (X). The safety device (1) further comprises a cap element (11) that can be arranged over the sleeve element (6) at least in portions, and by means of which the sleeve element (6) can be locked with respect to the movement of the syringe body (3) relative to the sleeve element (6). In this case, the sleeve element (6) and the cap element (11) are substantially cylindrical. The sleeve element (6) is shown again, in greater detail, in FIGS. 5 and 6 in an isometric view. FIG. 8 is a side view of the sleeve element (6), arranged on the syringe body (3). The cap element (11) is shown in detail in an isometric view in FIG. 7.

The locking in the axial direction is made possible by a projection (28) or a thicker portion at the distal end (4) of the syringe body, on which projection or thicker portion the distal end of the collar element (7) rests.

The collar element (7) is substantially formed as a hollow circular cylinder (12). The circular cylinder (12) comprises a lateral surface (12a), on which two guide projections (9) are arranged. The guide projections (9) extend radially outwards from the lateral surface (12a), and are diametrically opposed to one another. Furthermore, said guide projections are formed as circular cylinders or as pins. These two guide projections (9) are each guided substantially along the axial direction (X) in a guide track (10) of the sleeve element (6) when the syringe body (3) is moved relative to the sleeve element (6). Furthermore, the collar element (7) is arranged on the distal end region (8) of the syringe body (3) so as to be rotatable in a circumferential direction (U).

The cap element (11) comprises a piercing means protective device (13), in which the piercing means (5) can be arranged. Furthermore, the sleeve element (6) comprises a distal opening (14), the internal diameter (14a) of said distal opening (14) being larger than the external diameter (13d) of the piercing means protective device (13), such that the piercing means protective device (13) can be arranged inside the sleeve element (6).

In this case, the distal end (26) and an adjacent distal region of the piercing means (5) are arranged in a cavity of the piercing means protective device (13). The cavity comprises a first region (13a), the piercing means protective device (13) resting on the inner walls thereof in said first region. In a third region (13c) of the piercing means protective device (13), the cavity additionally extends over the distal end (4) of the syringe body. A second region (13b) is arranged between the first (13a) and the third region (13c), in which second region the internal diameter of the cavity increases from the first region (13a) to the third region (13c). The piercing means protective device (13) extends over the distal end region (8) of the syringe body (3) as far as the collar element (7). The piercing means protective device (13) is in operative contact with the collar element (7), as a result of which the collar element (7) can be locked with respect to a rotation.

The cap element (11) further comprises two diametrically opposed wing-like elements (17). This can also be seen in FIG. 7. Said wing-like elements (17) are complementary to the receptacles (18) of the sleeve element (6). The receptacles are formed as recesses in the sleeve element (6). This can also be seen in FIGS. 5 and 6. If the cap element (11) is arranged on the sleeve element (6), the two wing-like elements (17) can be received in the two receptacles (18) of the sleeve element (6). In this case, the piercing means protective device (13) extends through the distal opening (14) of the sleeve element (6). It would also be conceivable for at least one wing-like element (17) to be in operative contact with the collar element (7), as a result of which the collar element (7) can be locked with respect to a rotation.

The distal region (19) of the sleeve element (6) comprises the distal opening (14) of the sleeve element (6) and an annulus (30), which surrounds the distal opening (14) of the sleeve element (6). In this case, the external diameter of the annulus (30) is smaller than the external diameter of the adjacent region of the sleeve element (6). A first (30a) and a second front face (31) are thus formed on the sleeve element (6). The cap element (11) is correspondingly complementary, and therefore the distal region (20) of said element comprises contact surfaces (32) on the inside, which contact surfaces rest on the two front faces (30a, 31).

Figure 2:
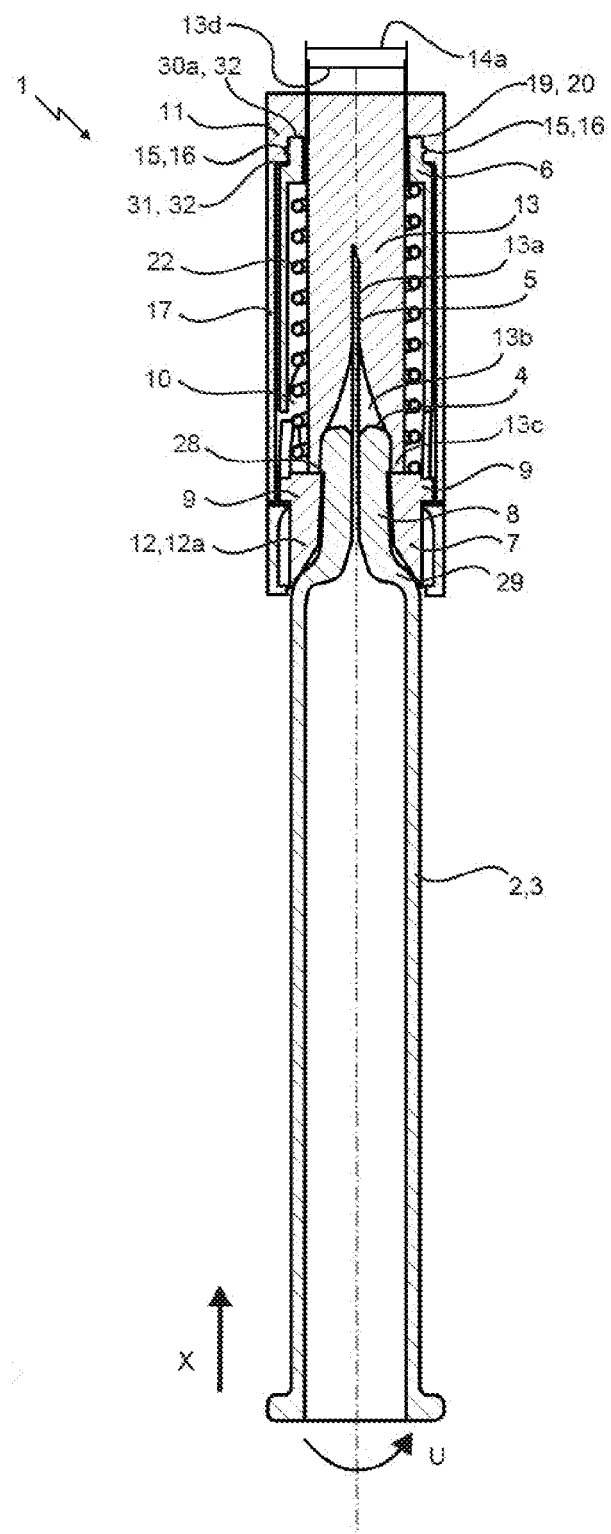
FIG. 2 is a sectional view of a syringe comprising a safety device according to a further embodiment.

FIGS. 1 and 2 show embodiments of the safety device (1) in which the cap element (11) is formed integrally with the piercing means protective device (13).

Figure 3:
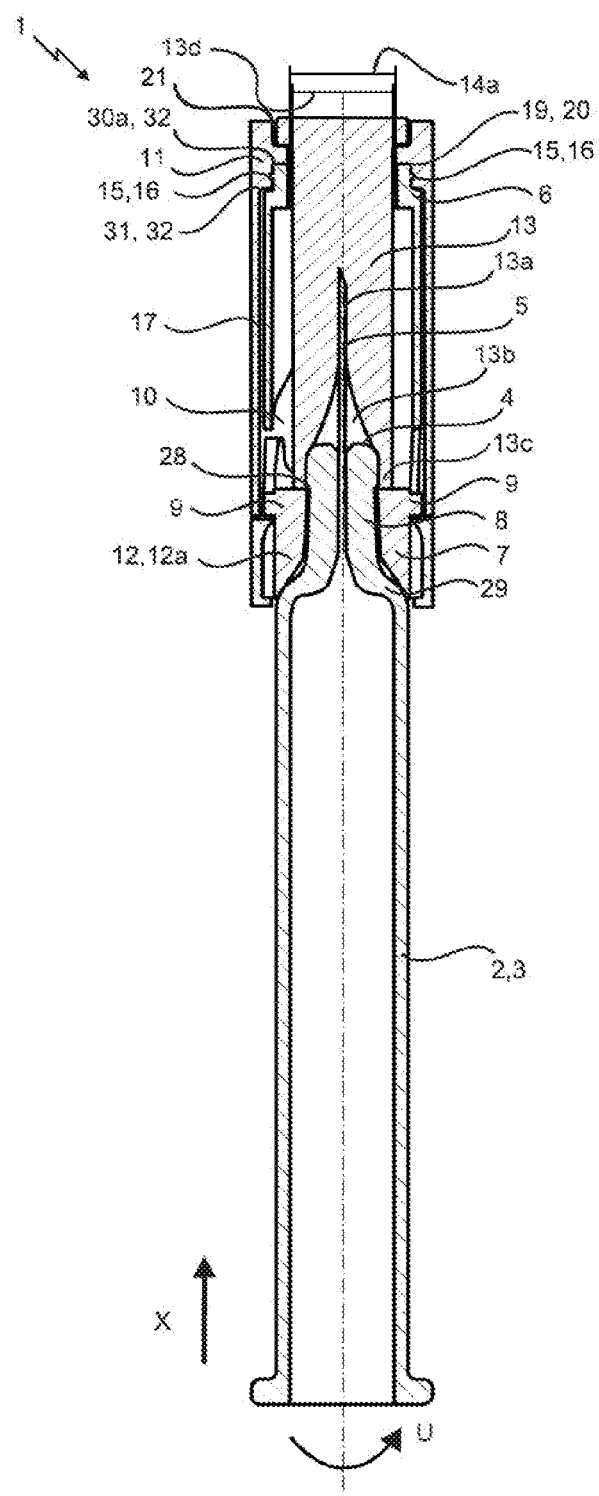
FIG. 3 is a sectional view of a syringe comprising a safety device according to a further embodiment.
Figure 4:
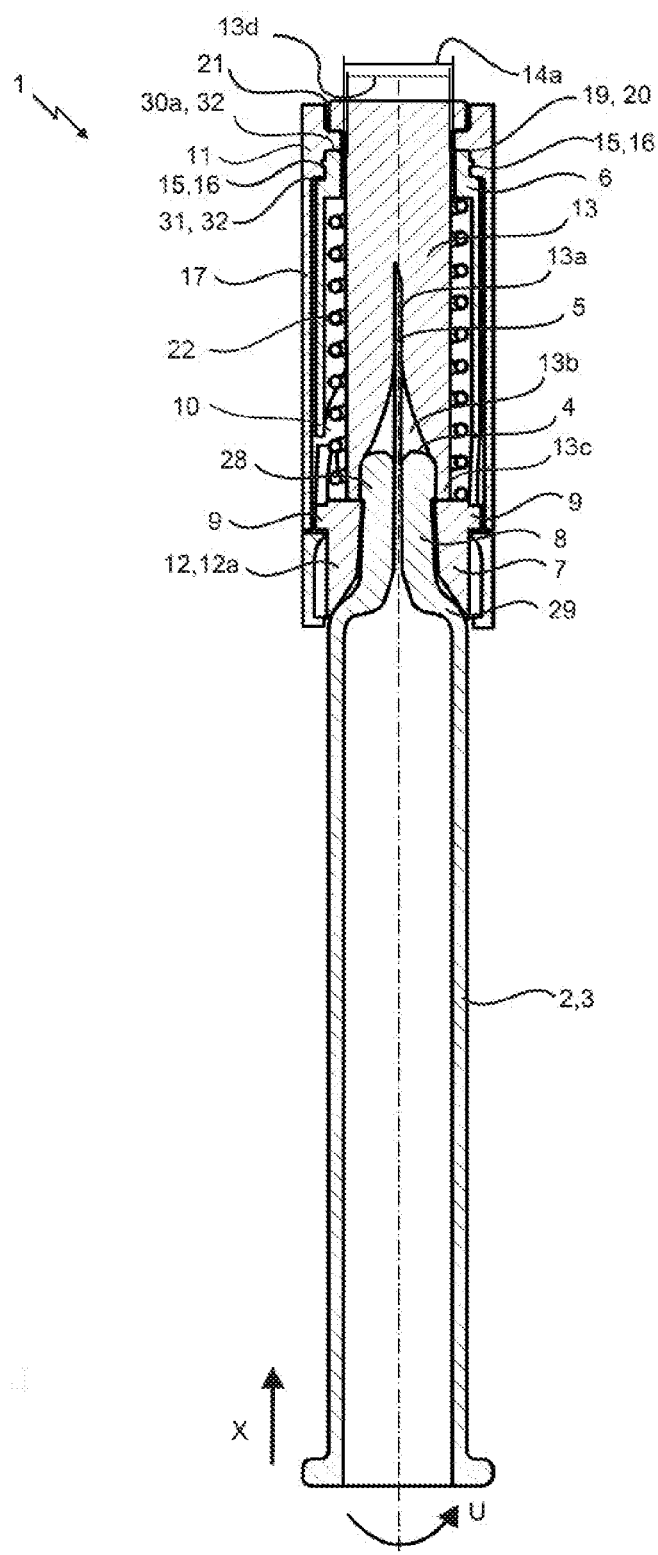
FIG. 4 is a sectional view of a syringe comprising a safety device according to a further embodiment.

FIGS. 3 and 4 show embodiments of the safety device (1) in which the cap element (11) comprises a distal opening (21). In this case, the distal opening (21) is formed as a receptacle in order to receive the piercing means protective device (13). The piercing means protective device (13) comprises a flange on the distal end thereof, which flange is embedded in the receptacle of the distal opening (21) of the cap element (11).

FIG. 2 and FIG. 4 again show a safety device (1), which comprises a spring element (22) in the form of a spiral spring, which is operatively connected to the syringe body (3) and counteracts the movement of the sleeve element (6) relative to the safety device (1). Accordingly, the piercing means (5) remains inside the sleeve element (6) until the intended use. During use, the sleeve element (6) has to be moved counter to the spring force in order for the piercing means (5) to be able to pass through the distal opening (14) of the sleeve element (6). After the syringe (2) has been used, the sleeve element (6) automatically slides over the piercing means (5) again, driven by the spring force of the spring element (22). The guidance of the guide projection (9) in the guide tracks (10) causes the collar element (7) to rotate counter to the circumferential direction (U). The user is thus protected from receiving stab wounds from the used and contaminated piercing means.

According to the embodiments shown in FIGS. 1 to 4 and 6, the cap element (11) and the sleeve element (7) comprise complementary latching elements (15, 16) so that the cap element (11) and the sleeve element (7) can be latched together in a separable manner. In the present embodiments, the sleeve element (6) comprises a distal region (19) on which latching elements (15) are arranged. These latching elements (15) can be latched into complementary latching elements (16) which are arranged in a distal region (20) of the cap element (11). In particular, the latching elements (15) of the sleeve element (6) are arranged on a lateral surface of the annulus (30).

Figure 5:
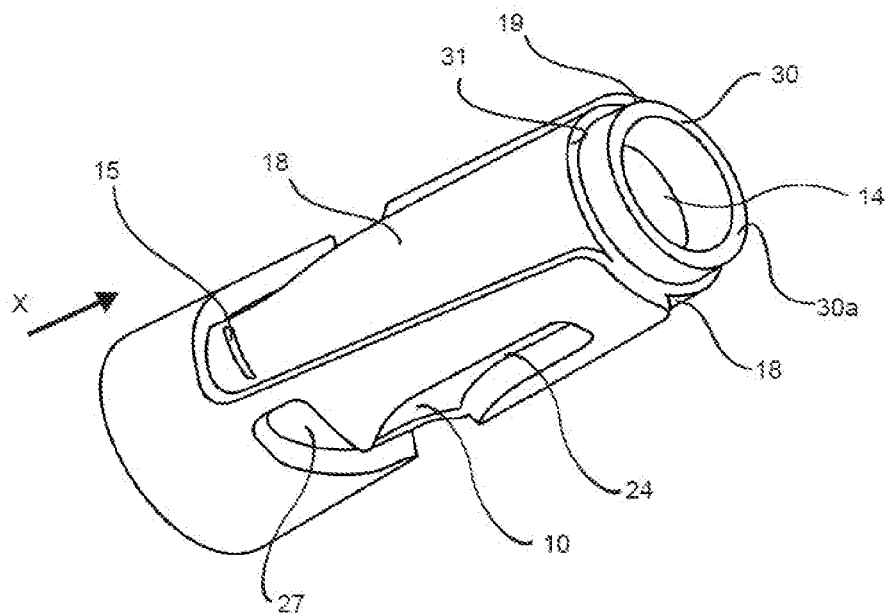
FIG. 5 is an isometric view of a sleeve element according to a further embodiment.

FIG. 5 shows a sleeve element (6) which comprises two receptacles (18) for the wing-like elements (17) of the cap element (11). Latching elements (15) are arranged in the receptacles (18), which latching elements are complementary to corresponding latching elements (16) of the wing-like elements (17) of the cap element (11) (not shown here), and can be latched therein.

The guide tracks (10) of the sleeve element (6) comprise a first (23) and a second trackregion (24), which are separated from one another by a fictive separating line (25) extending along the axial direction (X) of the syringe body (3), it being possible for the guide projection (9) to be arranged in a starting position in the first track region (23) and to be moved from the first track region (23) into an end position in the second track region (24) by passing the separating line (25) when a distal end (26) of the piercing means (5) is arranged at the level of the distal opening (14) of the sleeve element (6) as the syringe body (3) is moved relative to the sleeve element (6). This can be seen in FIGS. 5, 6 and 8, the guide projection (9) having passed the separating line (25) in FIG. 8, as a result of which the distal end (26) of the piercing means (5) is already protruding beyond the distal opening (14) of the sleeve element (6).

The sleeve element (6) further comprises an end region (27). In this case, the guide projections (9) can be moved, by means of a track of the second track region (24), from the second track region (24) into an end region (27). In this end region (27), a movement of the sleeve element (6) relative to the syringe body (3) is at least limited, substantially in the axial direction (X).

All of the features disclosed in the application documents are claimed to be essential to the invention provided that they are novel over the prior art, either on their own or in combination with one another.

LIST OF REFERENCE SIGNS 1 safety device
2 syringe
3 syringe body
4 distal end of the syringe body
5 piercing means
6 sleeve element
7 collar element
8 distal end region of the syringe body
9 guide projection
10 guide track
11 cap element
12 hollow circular cylinder
12a lateral surface of the circular cylinder
13 piercing means protective device
13a first region
13b second region
13c third region
13d external diameter
14 distal opening of the sleeve element
14a internal diameter
15 latching element
16 latching element
17 wing-like element
18 receptacle
19 distal region of the sleeve element
20 distal region of the cap element
21 distal opening of the cap element
22 spring element
23 first track region
24 second track region
25 separating line
26 distal end of the piercing means
27 end region
28 projection
29 transition region
30 annulus
30a first front face
31 second front face
32 contact surfaces
X axial direction
U circumferential direction

The invention claimed is:

1. A safety device for avoiding stab wounds for a syringe having a syringe body and a piercing means arranged at the distal end of the syringe body, said safety device comprising a sleeve element, which extends along an axial direction (X) and at least partially encloses the piercing means and the syringe body, and a collar element, which can be arranged on a distal end region of the syringe body and locks the safety device in the axial direction (X), the collar element comprising at least one guide projection, which engages in at least one guide track of the sleeve element, wherein:

the collar element is arranged on the distal end region of the syringe body so as to be rotatable in a circumferential direction (U) of the syringe body, wherein a movement of the syringe body along an axial direction (X) relative to the sleeve element and the guidance of the guide projection cause the collar element to rotate along the circumferential direction (U), wherein the safety device comprises a cap element that can be removably arranged over the sleeve element at least in portions, the cap element comprising a piercing means protective device, in which the piercing means can be arranged and which is arranged inside the sleeve element, wherein the piercing means protective device can be brought into operative contact with the collar element, wherein through said operative contact the collar element can be locked with respect to said rotation, wherein said lock of the collar element with respect to the rotation causes a lock of said movement of the syringe body relative to the sleeve element.

2. The safety device according to claim 1, wherein:
the collar element is substantially formed as a hollow circular cylinder, the circular cylinder comprising a lateral surface, on which the at least one guide projection is arranged.

3. The safety device according to claim 1, wherein:
the sleeve element comprises a distal opening, having an internal diameter larger than an external diameter of the piercing means protective device at least in portions, such that the piercing means protective device can be arranged inside the sleeve element.

4. The safety device according to claim 1, wherein:
the cap element and the sleeve element comprise complementary latching elements so that the cap element and the sleeve element can be latched together in a separable manner.

5. The safety device according to claim 1, wherein:
the cap element comprises at least one wing-like element which can be received in at least one receptacle of the sleeve element.

6. The safety device according to claim 5, wherein:
at least one wing-like element can be brought into operative contact with the collar element, as a result of which the collar element can be locked with respect to a rotation.

7. The safety device according to claim 5, wherein:
at least one latching element is arranged on the at least one wing-like element of the cap element, which latching element can be latched into at least one complementary latching element that is arranged in the at least one receptacle of the sleeve element.

8. The safety device according to claim 1, wherein:
the sleeve element comprises a distal region on which at least one latching element is arranged, it being possible for the at least one latching element to be latched into at least one complementary latching element that is arranged in a distal region of the cap element.

9. The safety device according to claim 1, wherein:
the cap element is formed integrally with the piercing means protective device.

10. The safety device according to claim 1, wherein:
the cap element comprises a distal opening, the distal opening being formed as a receptacle, in order to receive the piercing means protective device.

11. The safety device according to claim 1, wherein:
the safety device comprises at least one spring element, which is operatively connected to the syringe body and counteracts the movement of the sleeve element relative to the safety device.

12. The safety device according to claim 1, wherein:
the at least one guide track comprises a first and a second track region, which are separated from one another by a fictive separating line extending along the axial direction (X) of the syringe body, it being possible for the guide projection to be arranged in a starting position in the first track region and to be moved from the first track region into an end position in the second track region by passing the separating line when a distal end of the piercing means is arranged at the level of the distal opening of the sleeve element as the syringe body is moved relative to the sleeve element.

13. The safety device according to claim 12, wherein:
the at least one guide projection can be moved, by means of a track of the second track region, from the second track region into an end region in which a movement of the sleeve element relative to the syringe body is at least limited, substantially in the axial direction (X).

\* \* \* \* \*